US009314621B2

(12) United States Patent
Ronchetti et al.

(10) Patent No.: US 9,314,621 B2
(45) Date of Patent: Apr. 19, 2016

(54) METHOD FOR CONTROLLING AN ELECTROPORATION DEVICE

(75) Inventors: Mattia Ronchetti, Carpi (IT); Ruggero Cadossi, Carpi (IT); Donata Marazzi, Carpi (IT); Claudio Bertacchini, Carpi (IT)

(73) Assignee: Igea S.P.A., Carpi (IT)

( * ) Notice: Subject to any disclaimer, the term of this patent is extended or adjusted under 35 U.S.C. 154(b) by 114 days.

(21) Appl. No.: 14/114,192

(22) PCT Filed: Apr. 30, 2012

(86) PCT No.: PCT/IB2012/052159
§ 371 (c)(1),
(2), (4) Date: Jan. 6, 2014

(87) PCT Pub. No.: WO2012/147072
PCT Pub. Date: Nov. 1, 2012

(65) Prior Publication Data
US 2014/0148876 A1     May 29, 2014

(30) Foreign Application Priority Data

Apr. 29, 2011    (IT) .............................. TO2011A0374

(51) Int. Cl.
*A61N 1/30*        (2006.01)
*A61N 1/32*        (2006.01)

(52) U.S. Cl.
CPC ................ *A61N 1/327* (2013.01); *A61N 1/303* (2013.01); *A61N 1/325* (2013.01)

(58) Field of Classification Search
CPC ....... A61B 5/0424; A61N 1/327; A61N 1/325
See application file for complete search history.

(56) References Cited

U.S. PATENT DOCUMENTS

| 6,678,554 | B1 * | 1/2004 | Sun et al. ..................... 604/20 |
| 2005/0052630 | A1 * | 3/2005 | Smith et al. .................. 355/53 |
| 2008/0091135 | A1 * | 4/2008 | Draghia-Akli et al. ......... 604/20 |
| 2008/0208107 | A1 | 8/2008 | McRae et al. |

FOREIGN PATENT DOCUMENTS

| EP | 0 904 801 A2 | 3/1999 |
| WO | WO 00/62857 A1 | 10/2000 |

OTHER PUBLICATIONS

PCT Notification of Transmittal of the International Search Report and the Written Opinion of the International Searching Authority, or the Declaration for PCT Counterpart Application No. PCT/IB2012/052159, 13 pgs., (Aug. 20, 2012).

* cited by examiner

*Primary Examiner* — George Evanisko
(74) *Attorney, Agent, or Firm* — Blakely, Sokoloff, Taylor & Zafman LLP

(57) ABSTRACT

A method for controlling an electroporation device configured for supplying an electrical power signal to a plurality of pairs of electrodes coupled to a portion of the human body, wherein the following steps are performed: detecting, in the course of an electroporation treatment, a condition of malfunctioning or fail for the pairs of electrodes for which at least one electrical parameter of the power signal supplied to the electrodes themselves has an anomalous value; storing an indicator of the pairs of electrodes in the fail condition; and selecting the pairs of electrodes in the fail condition and re-computing new parameters in order to implement a subsequent electroporation process.

8 Claims, 2 Drawing Sheets

METHOD FOR CONTROLLING AN ELECTROPORATION DEVICE

CROSS-REFERENCE TO RELATED APPLICATIONS

This patent application is a U.S. National Phase Application under 35 U.S.C. §371 of International Application No. PCT/IB2012/052159, filed Apr. 30, 2012, entitled METHOD FOR CONTROLLING AN ELECTROPORATION DEVICE, which claims priority to Italian Patent Application No. TO2011A000374, filed Apr. 29, 2011.

TECHNICAL FIELD

The present invention relates to a method for controlling an electroporation device.

BACKGROUND ART

As is known, electroporation treatments are carried out using electronic devices designed to supply at output a pulsating a.c. signal to a plurality of electrodes applied to a tissue for creating currents induced in the tissue and modify the permeability of the cell membrane of the cells present in the tissue itself. The modification of the permeability of the cell membrane is normally used for carrying drugs, organic compounds, or generically molecules within the cell.

The parameters of the a.c. signal, for example the waveform, frequency, voltage, duty-cycle, and application time, are normally defined in an off-line mode, i.e., before starting the treatment, according to the effect that it is desired to obtain on the cells. Said definition includes the use of tables based upon experimental data, i.e., data that have been collected and refined by monitoring the results of a plurality of electroporation treatments performed previously.

Not always does the use of said experimental data enable execution of an electroporation treatment that obtains the desired effects. In the case of partial or total failure of the electroporation method, it is consequently difficult to determine what further actions to perform.

SUMMARY

The aim of the present invention is to provide a method for controlling an electroporation device that, in the case of failure, will enable automatic modification of the parameters of the treatment previously performed by computing and implementing new parameters.

The above aim is achieved by the present invention in so far as this relates to a method for controlling an electroporation device configured for supplying an electrical power signal to a plurality of pairs of electrodes coupled to a portion of the human body, the method comprising the steps of: detecting, in the course of an electroporation treatment, a condition of malfunctioning or fail for the pairs of electrodes for which at least one electrical parameter of the power signal supplied to the electrodes themselves has an anomalous value; storing an indicator of the pairs of electrodes in the fail condition; selecting the pairs of electrodes in the fail condition and re-computing for them new parameters for implementing a subsequent electroporation process.

BRIEF DESCRIPTION OF THE DRAWINGS

The invention will now be described with reference to the attached drawings, which illustrate an example of embodiment thereof and in which.

DETAILED DESCRIPTION

Figure 1:
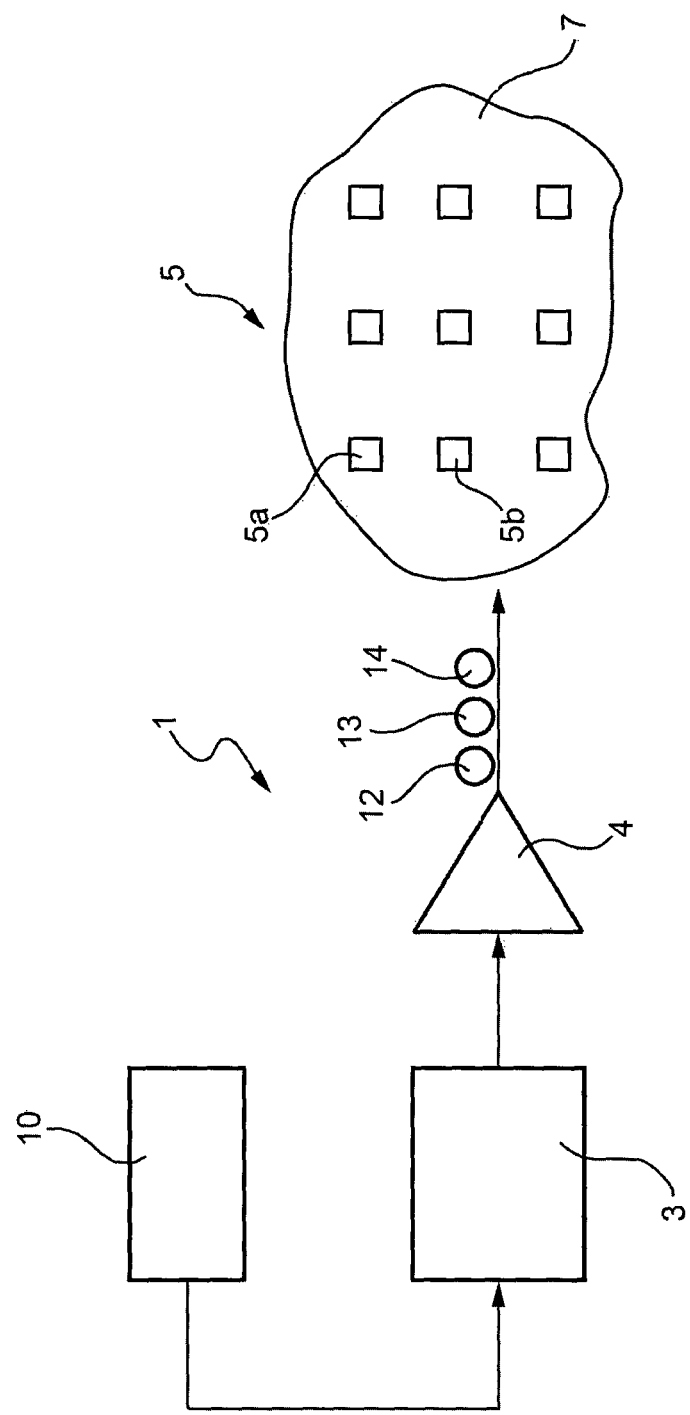
FIG. 1 illustrates, in a schematic way, an electroporation device operating according to the method according to the present invention.

In FIG. 1, designated as a whole by 1 and illustrated schematically is an electroporation device which comprises a hardware structure of a known type, in which a signal generator 3 of an adjustable type produces at output a pulsating signal that is supplied at input to a power amplifier 4, which in turn supplies a power signal to a set of electrodes 5 (for example, to a plurality of needle-shaped electrodes arranged according to an orderly array structure).

The electrodes 5 are designed to be applied to a portion of human body 7 for generating electrical fields designed to modify the permeability of the cell membrane of the cells comprised in the portion 7 and impinged upon by the electrical field. Typically, the power signal is supplied in sequence to different pairs of electrodes 5a, 5b so that the electrical field will impinge upon the entire portion 7 in which the electrodes 5 are arranged.

A control unit 10 of the signal generator 3 enables regulation of a plurality of parameters, amongst which:

the waveform of the power signal (for example, square-wave, sawtooth, sinusoidal, triangular, exponential, etc.);
the frequency of the power signal;
the duty-cycle of the power signal;
the application time of the power signal;
the temporal spacing between groups of consecutive pulses; and
other electrical parameters of the power signal.

The device 1 is provided with a plurality of sensors that monitor continuously the electrical quantities of the electroporation process in progress; in particular, sensors 12, 13, 14 are provided, designed to measure the instantaneous value of the current Ie supplied to each pair of electrodes 5a, 5b, the voltage value Ve applied to said pair of electrodes, and the impedance $Z(\omega)$ present between said pair of electrodes.

According to the present invention, the microprocessor unit of the control unit 10 implements a plurality of instructions that implement a control method, as described hereinafter with reference to FIG. 2.

In use, on the basis of the type of electroporation treatment to be carried out, by means of a calculation procedure of an off-line type, the distance between the electrodes 5 and their arrangement are set, and the characteristics of the power signal and the duration of the electroporation treatment are also defined. Typically, the setting is made with a set of maps (not illustrated) that take into account experimental data obtained from treatments performed previously.

The electroporation treatment starts. During said treatment the instantaneous values of the voltage Ve and of the current Ie are monitored continuously.

In the case where, for a given pair of electrodes, the value of current Ie departs from a range of acceptability (and, namely, is too high or too low) a situation of malfunctioning or fail is detected, for that pair of electrodes.

In the presence of an indication of fail the value of impedance $Z(\omega)$ present between the pair of electrodes considered is measured (said operation is indicated by block in FIG. 2) and an indicator (tag) is stored, which identifies the pairs of electrodes 5 that have given rise to a fail.

The control method according to the present invention performs, for the pairs of electrodes for which a fail has been detected and a tag has been stored, a further analysis (said operations are indicated by the respective block 90 and 60 in FIG. 2) described hereinafter with reference to FIG. 2.

Figure 2:
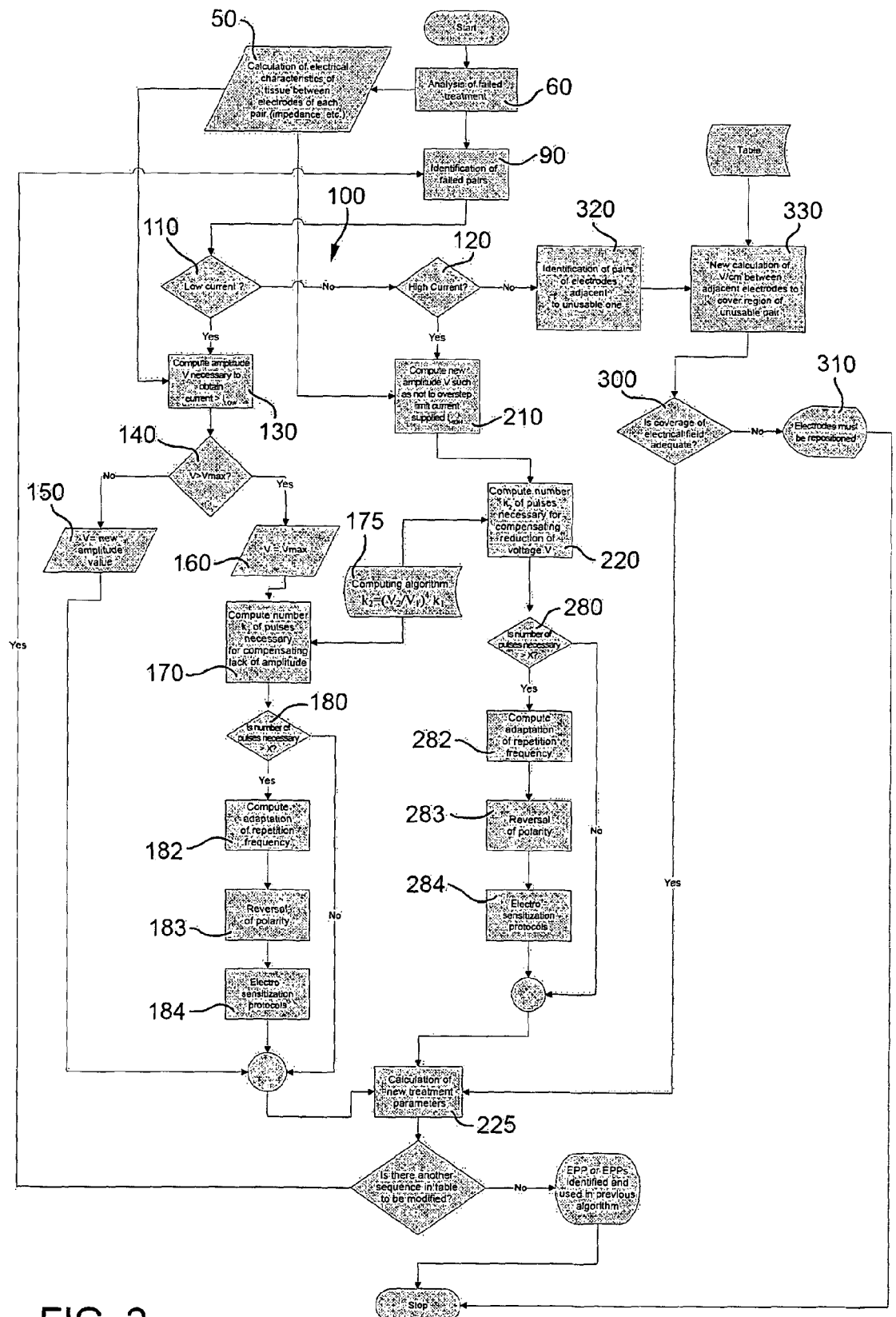
FIG. 2 illustrates by means of a block diagram the method according to the present invention.

With particular reference to FIG. 2, the method comprises a block 100 (subsequent to block 90), which, since parameters of the electroporation process have been detected outside an interval of acceptability for a pair of electrodes selected (block 90—Identification of failed pairs), performs an analysis for defining the type of corrective action for said pair of electrodes. The pair of electrodes in question is again supplied with the power signal for verifying the value of the electrical quantities associated thereto.

In this connection, block 100 comprises a block 110 that verifies whether the current that has been supplied to the electrodes $I_E$ is lower than a minimum threshold value $I_{LOW}$; if it is not (i.e., if the current $I_E$ is higher than the threshold value $I_{LOW}$) the current is recognized as acceptable, and block 110 is followed by a block 120; otherwise (i.e., if the current $I_E$ is lower than the threshold value $I_{LOW}$), an anomalous current is recognized, which is an index of an electroporation process that has not yet started, and from block 110 control passes to block 130.

Block 130 computes (in a known way by applying Ohm's law once the impedance $Z(\omega)$ is known) the value of the voltage that can be applied to the electrodes necessary to obtain an increase of the current and bring the electroporation current to a target value (for example, at least 1.5 A). The calculation made in block 130 is possible in so far as the impedance of the tissue is known precisely.

Processing of block 130 continues until a current is calculated having a target value $I_{TARGET}$ corresponding to which is a voltage $V_T$ necessary to obtain said value of current.

Next, a check is made (block 140 subsequent to block 130) to verify whether the voltage $V_T$ thus obtained is lower than (or equal to) the maximum voltage $V_{Max}$ that can be supplied by the electroporation device 1; if so (i.e., in the case where the voltage calculated can be supplied by the device that implements the electroporation method, i.e., $V_T < V_{Max}$) block 140 is followed by a block 150 that stores the voltage equal to $V_T$ to be applied for the pair of electrodes considered. The parameters of the electroporation process are thus redefined (block 225), and the verification process continues for each other pair of electrodes for which a fail condition has been detected (consequently control returns to block 90).

In the case where the voltage $V_T$ thus obtained is higher than the maximum voltage $V_{Max}$ that can be supplied, block 140 is followed by a block 160, which detects said physical limit in the voltage that can be supplied to implement a series of solutions aimed at obtaining in any case electroporation of the tissue. In this connection, block 160 is followed by a block 170 that calculates the number of pulses per unit time (for example, the treatment time) necessary to obtain electroporation of the tissues having available the voltage $V_{Max}$; in particular, the number of pulses supplied per unit time is increased bringing the current number of pulses $N_{PULSE}$ to a higher number $K_{PULSE}$ (with $K_{PULSE} > N_{PULSE}$); the number of pulses per unit time is thus increased. The calculation of the number of pulses $K_{PULSE}$ necessary is carried out by a block 175 on the basis of an algorithm.

The algorithm of block 175 envisages calculation of the equivalent dose EqD absorbed by the means, according to the formula $$\mathrm{EqD} = \tau E^2 t k^{-1/2} \rho^{-1} \quad [1]$$

where $\tau$ is the conductivity of the tissue, E the electrical field supplied, t the time duration of each pulse, k the number of pulses supplied, and $\rho$ the density of the material.

Said equivalent dose is calculated first for the standard condition, i.e., the one that is determined by the protocol previously applied with parameters of the signal (for example, waveform, frequency, voltage, duty-cycle, application time) defined in an off-line mode and that has given rise to the fail condition.

In the present case, since the intensity $E^2$ of the electrical field is no longer modifiable (block 160, the voltage reached is the limit voltage), it is alternatively possible to modify the number of pulses $k^{-1/2}$ so as to maintain the equivalent dose EqD constant and equal to the one obtained in the calculation executed for the standard condition.

Consequently, the number k of the pulses is given by $$\mathrm{EqD} = \tau E 2 t k - 1/2 \, \rho - 1 \quad (1)$$

For completeness, given that it is one and the same tissue, Equation 1 can be simplified as follows $$E_1^2 k_1^{-1/2} = E_2^2 k_2^{-1/2}$$

Since E=V/d, if we assume maintaining the same geometry of the electrodes, it can be further simplified as follows $$V_1^2 k_1^{-1/2} = V_2^2 k_2^{-1/2}$$

$$k_{PULSE} = (V_2/V_1)^4 k_1$$

In the case where the number of pulses necessary $K_{PULSE}$ is lower than a threshold value X (said control is performed by a block 180 subsequent to block 170 that carries out the operation $K_{PULSE} < X$), stored as electroporation parameter is the value $K_{PULSE}$ of pulses having a voltage equal to the maximum value that can be supplied by the machine (block 225), and the verification process continues for another pair of electrodes for which a fail condition has been detected.

In the case where the number of pulses necessary $K_{PULSE}$ is higher than X, stored as electroporation parameter is the value X (block 182) of pulses having a voltage equal to the maximum value that can be supplied by the machine, and the verification process continues for another pair of electrodes for which a fail condition has been detected.

In the case where the maximum value of pulses X is detected, also a request for reversal of polarity of the power signal can be stored (block 183). Alternatively, the reversal of polarity can be carried out in any case irrespective of whether X is exceeded.

If necessary, other electro-sensitization techniques (block 184) can also be applied, i.e., techniques that increase the sensitivity of the tissues to the electroporation phenomenon, for example by dividing the number of pulses thus calculated into a number of applications separated by intervals in which no pulse is supplied (for example, 30 seconds-30 minutes).

All the parameters modified are stored, and the verification process continues for another pair of electrodes for which a fail condition has been detected.

Block 120 verifies whether the electroporation current $I_E$ exceeds a maximum value $I_{HIGH}$ beyond which the electroporation device cannot operate in safety conditions.

In the case where the current $I_E$ exceeds the maximum value $I_{HIGH}$, the process continues with a block 210 subsequent to block 120 that calculates a reduced voltage value $V_{min}$ that enables a reduction in the current such that the value of current $I_E$ drops below the maximum value $I_{HIGH}$ according to Ohm's law given that the impedance of the tissue is known.

Block 210 is followed by a block 220 that calculates the increase in the numbers of pulses necessary per unit time (for example, treatment time) in order to compensate for the reduction in voltage performed in block 210.

A value $K_{COMP}$ of pulses is calculated with procedures (block 222) altogether similar to those of block 175 and consequently, for simplicity, not described in detail.

In the case where the number of pulses necessary $K_{COMP}$ is lower than a threshold value X (said control is performed by a block 280 subsequent to block 270 that carries out the operation $K_{PULSE}<X$) stored as electroporation parameter is the value $K_{PULSE}$ of pulses having a reduced voltage $V_{min}$ equal to the one calculated by block 210, and the verification process continues for another pair of electrodes for which a fail condition has been detected (block 225).

In the case where the necessary number of pulses $K_{COMP}$ is higher than X, the maximum value X of pulses having a voltage corresponding to the reduced voltage $V_{min}$ is stored (block 282) equal to the one calculated by block 210, and the verification process continues for another pair of electrodes for which a fail condition has been detected after a series of corrective actions have been attempted.

In fact, in the case where the maximum value of pulses X is detected, it is possible to store also a request for reversal of polarity (block 283) of the power signal. Alternatively, the reversal of polarity can be carried out in any case irrespective of whether X has been exceeded.

If necessary, it is also possible to apply other electro-sensitization techniques (block 284), i.e., techniques that increase the sensitivity of the tissues to the electroporation phenomenon, for example by dividing the number of pulses thus calculated into a number of applications separated by intervals in which no pulse is supplied (for example, 30 seconds-30 minutes).

All the parameters modified are stored (block 225), and the verification process continues for another pair of electrodes for which a fail condition has been detected.

The condition whereby the current does not exceed the threshold (output NO from block 120) is considered a non-realizable condition in so far as—in the case of presence of a current that is in any case acceptable—the fail condition would not arise.

A different output from block 120 is only possible when the post-pulse analysis detects a condition of overcurrent due to short circuit between the electrodes of a pair and not to a low-impedance load (transition from block 120 to block 210). It is possible to establish a minimum impedance below which this condition arises.

In the above case of short circuit, it is possible to resort to identification (block 320 subsequent to block 120) of a pair of electrodes different from the short-circuited one. From block 320 control then passes to a block 330 where the parameters of the pair identified are modified to increase the coverage of the electrical field so as to compensate for the absence of the short-circuited pair. In the case where the activity of compensation is not effective, from block 330 control goes to a block 300, which, in second instance, identifies all the pairs adjacent to the short-circuited one so as to modify the parameters of said pairs and increase the coverage of the electrical field in order to compensate for the absence of the short-circuited pair.

In the case where this procedure were to prove impracticable, a warning may be issued to signal the need to reposition the electrodes (block 310).

What is claimed is:

1. A method for controlling an electroporation device configured for supplying an electrical power signal to a plurality of pairs of electrodes coupled to a portion of the human body, the method comprising:
   detecting, in the course of an electroporation treatment, a condition of malfunctioning or fail for one or more pairs of electrodes for which at least one electrical parameter of the power signal supplied to the one or more pairs of electrodes has an anomalous value;
   storing an indicator of the one or more pairs of electrodes in the fail condition; and
   selecting the one or more pairs of electrodes in the fail condition and re-computing, for each of the one or more pairs, new parameters for implementing a subsequent electroporation process, wherein the operation of re-computing the new parameters comprises:
     re-applying said power signal to said one or more pairs of electrodes in the fail condition,
     verifying the value of the current thus supplied to the one or more pairs of electrodes,
     when said current is lower than a given threshold, calculating a voltage value configured for enabling an increase of the current to bring the current to a target value and comparing said voltage value with a threshold value, and
     when the voltage value is lower than the threshold value, storing said voltage value as a new electroporation parameter, and
     when the voltage value is not lower than the threshold value, adopting one or more corrective actions.

2. The method according to claim 1, wherein said detecting, in the course of an electroporation treatment, a condition of malfunctioning or fail comprises detecting whether the current supplied to the electrodes departs from a range of acceptability.

3. The method according to claim 1, wherein re-computing new parameters comprises:
   detecting the impedance existing between the one or more pairs of electrodes for which a condition of fail has been detected; and
   re-computing the parameters of the subsequent electroporation process on the basis of said impedance.

4. The method according to claim 1, wherein said corrective actions comprise at least one of the following operations:
   increasing a number of pulses contained in the power signal;
   reversing polarity of the power signal; and
   applying one or more electro-sensitization techniques.

5. The method according to claim 1, wherein re-computing new parameters comprises:
   re-applying said power signal to said one or more pairs of electrodes in the fail condition;
   verifying the value of the current supplied to the one or more pairs of electrodes;
   in the case where said current is higher than a given threshold, computing a voltage value configured for enabling a reduction of the current to bring the current to a value equal to or lower than a target value; and
   storing said voltage value as a new electroporation parameter.

6. The method according to claim 5, wherein the corrective actions that are adopted are configured to compensate for the reduction in voltage.

7. The method according to claim 6, wherein said corrective actions comprise at least one of the following operations:
   increasing a number of pulses contained in the power signal;

reversing polarity of the power signal; and applying one or more electro-sensitization techniques.

8. An electroporation device comprising:
a plurality of pairs of electrodes;
a power supply for providing an electrical power signal; and
an electronic control unit connected to the electrodes and the power supply to apply the electrical power signal as an electroporation treatment to at least one pair of the plurality of electrodes, the electronic control unit configured to perform a method comprising:
detecting, in the course of an electroporation treatment, a condition of malfunctioning or fail for one or more pairs of electrodes for which at least one electrical parameter of the power signal supplied to the one or more pairs of electrodes has an anomalous value;
storing an indicator of the one or more pairs of electrodes in the fail condition; and
selecting the one or more pairs of electrodes in the fail condition and re-computing for each of the one or more pairs, new parameters for implementing a subsequent electroporation process, wherein re-computing the new parameters comprises:
re-applying said power signal to said one or more pairs of electrodes in the fail condition,
verifying the value of the current thus supplied to the one or more pairs of electrodes,
when said current is lower than a given threshold, calculating a voltage value configured for enabling an increase of the current to bring the current to a target value and comparing said voltage value with a threshold value, and
when the voltage value is lower than the threshold value, storing said voltage value as a new electroporation parameter, and
when the voltage value is not lower than the threshold value, adopting one or more corrective actions.

* * * * *